United States Patent
Hill et al.

(10) Patent No.: US 8,571,803 B2
(45) Date of Patent: Oct. 29, 2013

(54) SYSTEMS AND METHODS FOR MODELING AND ANALYZING NETWORKS

(75) Inventors: Colin C. Hill, Somerville, MA (US); Bruce W. Church, Lawrence, MA (US); Paul D. McDonagh, Winchester, MA (US); Iya G. Khalil, Boston, MA (US); Thomas A. Neyarapally, Boston, MA (US); Zachary W. Pitluk, New Haven, CT (US)

(73) Assignee: Gene Network Sciences, Inc., Cambridge, MA (US)

( * ) Notice: Subject to any disclaimer, the term of this patent is extended or adjusted under 35 U.S.C. 154(b) by 1362 days.

(21) Appl. No.: 11/985,618

(22) Filed: Nov. 15, 2007

(65) Prior Publication Data

US 2008/0208784 A1 Aug. 28, 2008

Related U.S. Application Data

(60) Provisional application No. 60/859,057, filed on Nov. 15, 2006, provisional application No. 60/859,334, filed on Nov. 16, 2006, provisional application No. 60/899,696, filed on Feb. 6, 2007, provisional application No. 60/898,915, filed on Feb. 1, 2007, provisional application No. 60/902,446, filed on Feb. 21, 2007, provisional application No. 60/920,887, filed on Mar. 31, 2007, provisional application No. 60/923,950, filed on Apr. 17, 2007, provisional application No. 60/925,988, filed on Apr. 24, 2007, provisional application No. 60/965,682, filed on Aug. 21, 2007.

(51) Int. Cl.
*G06F 7/00* (2006.01)

(52) U.S. Cl.
USPC .................. 702/19; 702/20; 703/11; 707/700

(58) Field of Classification Search
None
See application file for complete search history.

(56) References Cited

PUBLICATIONS

Christopher et al. 2004; Ann N.y. Acad Sci 1020: 132-153.*

* cited by examiner

*Primary Examiner* — Mary Zeman
(74) *Attorney, Agent, or Firm* — Ropes & Gray LLP

(57) ABSTRACT

The systems and methods described herein utilize a probabilistic modeling framework for reverse engineering an ensemble of causal models, from data and then forward simulating the ensemble of models to analyze and predict the behavior of the network. In certain embodiments, the systems and methods described herein include data-driven techniques for developing causal models for biological networks. Causal network models include computational representations of the causal relationships between independent variables such as a compound of interest and dependent variables such as measured DNA alterations, changes in mRNA, protein, and metabolites to phenotypic readouts of efficacy and toxicity.

24 Claims, 7 Drawing Sheets

SYSTEMS AND METHODS FOR MODELING AND ANALYZING NETWORKS

CROSS-REFERENCE TO RELATED APPLICATIONS

This application claims the benefit of U.S. Provisional Patent Application Ser. No. 60/859,057, filed on Nov. 15, 2006, U.S. Provisional Patent Application Ser. No. 60/859,334, filed on Nov. 16, 2006, U.S. Provisional Patent Application Ser. No. 60/899,696, filed on Feb. 6, 2007, U.S. Provisional Patent Application Ser. No. 60/898,915, filed on Feb. 1, 2007, U.S. Provisional Patent Application Ser. No. 60/902,446, filed on Feb. 21, 2007, U.S. Provisional Patent Application Ser. No. 60/920,887, filed on Mar. 31, 2007, U.S. Provisional Patent Application Ser. No. 60/923,950, filed on Apr. 17, 2007, U.S. Provisional Patent Application Ser. No. 60/925,988, filed on Apr. 24, 2007, and U.S. Provisional Patent Application Ser. No. 60/965,682, filed on Aug. 21, 2007, the entire contents of each of which are incorporated herein by reference.

GOVERNMENT CONTRACT

The U.S. Government has a paid-up license in this invention and the right in limited circumstances to require the patent owner to license others on reasonable terms as provided for by the terms of Grant No. DE-FG02-04ER63806 awarded by the Department of Energy.

FIELD OF THE INVENTION

This invention generally relates to data-driven systems and methods for determining the mechanism of interaction of elements in networks such as biological networks.

BACKGROUND OF THE INVENTION

Selection of drug candidates for clinical development is a particularly difficult problem because there is generally a poor understanding of the biochemical pathways that determine the drug mechanisms of efficacy and toxicity. These biochemical pathways include, among other things, a series of biomolecules that may be suitable targets for drug development. For example, biomolecules such as kinases play a role in normal homeostasis and disease progression, often becoming deregulated through genetic alterations that result in their aberrant activities and/or changes in their overall expression. Even though kinases are easy targets for drug development, very few kinases inhibiting drugs are being developed. This is because the known mechanisms of action of these few drugs were based on the existence of decades of research and knowledge that is difficult to replicate in a short period of time.

High-throughput measurements of mRNA, protein and metabolite levels in conjunction with traditional dose-dependent efficacy and toxicity assays, has emerged as a means for elucidating drug or compound mechanism of action. Scientists have attempted to combine information from these measurements with knowledge about pathways from literature to assemble relevant biochemical pathways. Researchers then use numerical and statistical techniques such as clustering and statistical mining to distill through large quantities of data to understand and describe mechanisms of action.

Most of these approaches typically calculate covariances between the measurements (e.g., gene expression levels) and thereby reveal underlying correlations. However, such correlations are not helpful in making formal predictions that can be tested experimentally. For example, it may be possible for a gene to have a high expression level when another gene also has a high expression level. However, the genes may not be part of the same biochemical pathway and may be simply correlated with one another, while not being causally connected to each other. It would then be impossible to predict a change in gene expression in one gene based on the level of expression of the other. Furthermore, the published literature has only a small percentage of the molecular circuitry mapped out and can therefore only provide limited assistance to the researcher. Moreover, current techniques are not equipped to handle simultaneously different types of data including gene expression, proteomic, metabalomic, and other phenotypic data.

Researchers have begun applying a number of computational approaches to overcome some of the drawbacks noted earlier. These computational approaches attempt to reverse engineer gene and protein networks from molecular profiling data. However, because of the mathematical complexity of managing and resolving networks from such large data sets, these techniques are focused on networks with very few components.

Accordingly, there is a need for systems and methods for identifying and constructing models of compound mechanisms of action and extracting information from such models for selecting drugs for development. Generally, there is a need for systems and methods for inferring network models from large quantities of differing types of data and extracting information from such models.

SUMMARY OF THE INVENTION

The correlative approaches currently used to study biological systems using large quantities of biological data do not yield causal relationships between various proteins, metabolites, membranes and nucleic acids and other bio markers. Causality in biological systems is sometimes assigned by a scientist studying the system at hand as an inferred property based on the correlations. However, such methods of assigning causality are difficult to replicate and test objectively.

In accordance with the principles of the present invention, systems and methods for deriving causal models of networks are provided. For purposes of clarity, and not by way of limitation, the systems and methods may sometimes be described herein in the context of biological systems particularly with reference to drug discovery and development. However, it may be understood that the systems and methods of the present invention may be applied to any other system, including financial and communication networks.

The systems and methods described herein include data-driven techniques for developing causal models for biological networks. Causal network models include computational representations of the causal relationships between independent variables such as a compound of interest and dependent variables such as measured DNA alterations, changes in mRNA, protein, and metabolites to phenotypic readouts of efficacy and toxicity.

More particularly, the systems and methods described herein utilize a probabilistic modeling framework for reverse engineering an ensemble of causal models, from data.

The systems and methods described herein include methods of building a computer model to extract information from a dataset comprised of two or more variables. The methods include inferring said computer model containing equations describing the relationships between said variables, simulating said computer model to predict the impact of the change made to the value of one or more first variables on the values of one or more second variables. In certain embodiments, the simulation includes the implementation of a computer script to automatically change the value of one or more said first variables and record or display the resulting values of one or more second variables in the simulation. In certain embodiments, the score methods may include a Bayesian scoring method.

In certain embodiments, inferring a computer model includes building local models by selecting a set of interaction forms to define the quantitative relationships between variables in said local models, building local models by proposing connections between two or more of said variables and using a scoring method to determine how likely such local models are given the data. The methods further includes creating a library of local models ranked according to a score generated by said scoring method and building global models by choosing local models from said library of local models and connecting said local models. In such embodiments, building of local models may be achieved by a global optimization method such as metropolis Monte Carlo. In certain embodiments, inferring a computer model includes a constraining a search space using prior information about the variables in the dataset. Other techniques for inferring a model and performing data-driven simulations may be obtained from U.S. Patent Publication Nos. 2003/0144823, 2004/0243354 and 2004/0088116, the entire contents of each of which are incorporated herein by reference.

The method may further include displaying the values of some or all or substantially all of the variables in said model on top or next to their corresponding representation in a graphical depiction of said model. The graphical depiction (or graphical representation) may be a directed acyclic graph. In certain embodiments, the model may be represented using Diagrammatic Cell Language as described in U.S. Pat. No. 7,089,168, the entire contents of which are incorporated herein by reference. The model may be a consensus model comprised of two or more underlying models that together reflect the process that gave rise to the dataset. In certain embodiments, the model created contains variables reflecting two or more types of measurements including, but not limited to, genes, proteins, clinical measurements.

In certain embodiments, the information to be extracted is the mechanism of action of a drug in a biological system and the dataset comprises two or more variables measuring the activity of the drug in said biological system. The information to be extracted may be the identity of one or more biomarkers in a biological system and the dataset may comprise two or more variables measuring the activity of a drug in the biological system. In certain embodiments, the information to be extracted is the one or more pathways that connect the drug to the one or more second variables through the one or more first variables. The information to be extracted may include the mechanism of toxicity of a drug in a biological system and the dataset comprises two or more variables measuring the activity of the drug in said biological system. The information to be extracted may be the identity of one or more drug targets in a biological system. The information to be extracted may also be the genetics-dependent mechanism of efficacy, mechanism of toxicity, or biomarkers of efficacy or toxicity with respect to the use of one or more drugs in the biological system. The systems and methods described herein include methods for treating a disease by administering to an animal or human a therapeutic that binds to or otherwise affects the activity of the identified drug target.

In certain embodiments, the dataset has been taken from measurements of the activity of a biological system. The biological system may include a cell line, an animal, or a human. In one embodiment, the dataset may include data reflecting the use of two or more drugs in the same biological system. In such an embodiment, the information to be extracted may be the mechanism of action of the two or more drugs working together in said biological system. In another embodiment, the information to be extracted is the mechanism of toxicity of the two or more drugs when used together in said biological system. The dataset may also include two or more variables measuring the activity of the drug in the biological system. The information to be extracted may be the identity of one or more biomarkers of the two or more drugs' efficacy together in a biological system. In certain embodiments, multiple models are inferred from said dataset, wherein each of said multiple models reflects the process giving rise to the dataset, and said multiple models are simulated to produce a distribution of values for each of said second variables.

In certain embodiments, the dataset comprises data describing the values of various financial measures and said second variable or variables constitute one or more financial variables to be predicted for purposes of trading the securities relating to those variables. The aid one or more second variables may be prices or returns of securities to be traded. The dataset may comprise data describing an individual's behavior and past credit history, and said second variable or variables describe the likelihood of a fraudulent transaction or default. The dataset may also comprise data describing Internet searches and advertising revenue derived from such searches, and said one or more second variables describe advertisements viewed or advertising revenue. In certain embodiments, said dataset comprises two or more individuals' preferences regarding a good or service, said model contains the connections between preferences such that a user of said model can simulate the model to predict the likelihood of an individual preferring one or more second goods or services given that individual's preference of one or more first goods. The dataset may include data describing one or more physiological measures of brain activity and measures of behavior observed during or after said brain activity and said one or more second variables describe said behavior.

In certain embodiments, aid dataset comprises data describing the allocation of resources in a budget and one or more outcomes observed after said budget is implemented, and said one or more second variables describe said outcomes. The dataset may additionally comprise data regarding the behavior of third parties and external market forces. The dataset may comprise data describing the performance of one or more sports or game players and the compensation paid to one or more players, and said model is used to assemble an optimal team given a specified total team compensation. In certain embodiments, the dataset comprises data describing the performance of one or more sports or game players, and said model is simulated to provide outcomes for a computer game.

Additionally and optionally, the dataset may comprise one or more measures of customers' experiences and one or more measures of the performance of one or more businesses serving said customers, and said one or more second variables are measures of customer experience. The data set may comprise or more measures of customers' experiences and one or more measures of the performance of one or more businesses serving said customers, and one or more measures of said businesses' economic performance and said one or more second variables are measures of said businesses' economic performance.

The dataset comprises one or more measurements taken from patients and said model is used to identify one or more molecules to be targeted with a patient. In such embodiments, one or more databases are provided that contain the molecules targeted by one or more drugs in development or on the market, and said one or more molecules to be targeted are searched for in said one or more databases to identify one or more drugs to treat said patient. The dataset may also comprise data derived from patients' tumor biopsies combined with data derived from patients' tumors implanted in mice.

In certain embodiments, one or more of the models is used to predict the most optimal one or more targets for a patient, by providing a dataset comprised of two or more patients' data, building one or more models, and simulating said models to determine which variables in the model, when changed, have the greatest impact on the output variables.

In certain embodiments, the dataset may include measurements of the activity or abundance of one or more biomolecules in an animal and one or more associated clinical outcomes, and said model is used to predict the animal's clinical outcome. The dataset may include parameter data, the connections between variables are unknown, and the models are used to determine the values of the parameters.

In certain embodiments, the dataset may include data from two or more patients and contains differences between said two or more patients. In such embodiments, the differences exist with respect to one or more of the following: genes, regions of DNA, RNA, miRNA, proteins, modified proteins, and clinical endpoints. A patient's outcome may be predicted by inputting one or more input variables for such patient and simulating the model.

In certain embodiments, one or more models created using the methods described herein are combined with one more models built by other methods, wherein each of said models is represented in the same or similar format to enable such combination.

The dataset may include a proteomics dataset, and one or more outlier data points are removed from said dataset. The methods may further comprise regressing the theoretical estimated distribution of protein concentrations against observed values, identifying outlier data points as data points having significant influence in the estimation of the parameters of the log-normal distribution, removing said outlier data points from the dataset, recalculating the parameters of the distribution, and replacing said outlier data points with the maximum likelihood estimate for the distribution.

In another aspect, the systems and methods described herein include methods and systems for treating a patient including a computer system for building and simulating a biological model and an interface for allowing a clinician to query the computer system. In certain embodiments, the computer system is configured with hardware and/or software to determine tests to be administered to a patient, patient's diseases and the corresponding models of biological mechanism of disease and drug action.

In another aspect, the systems and methods described herein include methods for selecting one or more treatments for a patient. The methods include determining which one or more therapeutics should be selected by simulating second models reflecting the effectiveness of said therapeutics given certain patient-specific input conditions, in said second model or models, observing whether said patient-specific conditions result in a prediction that the one or more therapeutics will be effective in said patients, reporting said prediction to said clinicians, and optionally repeating said method if the prediction is that the treatment will not be effective or if the initially predicted treatment is not effective.

In still another aspect, the systems and methods described herein include methods for building a model of dose-response variability from animals administered the same dose of a therapeutic. The methods include building models from a dataset comprised of dose-response data from more than one animal, and further comprising the use of the amount of the therapeutic circulating in the bloodstream to represent the dose in said dataset.

In yet another aspect, the systems and methods described herein may be used to reduce the number of clinical trial cohorts required to establish a dose-response relationship of drugs. In such aspects, the systems and methods described herein may establish a dose-response relationship using data from one or more cohorts.

In another aspect, the systems and methods described herein may include methods for identifying molecules causally related to clinical outcomes for animal subjects. The methods may include generating molecular profiling data from biological samples from said animals and adding said molecular profiling data to said dataset, conducting genotyping data from biological samples from said animals and adding said genotyping data to said dataset, generation of clinical data from said animals and adding said clinical data to said dataset, conducting quantitative trait locus analysis to identify QTL hotspots, inferring said model using a dataset comprising said QTL hotspots, said molecular profiling data, said genotyping data, and said clinical data, and simulating said model.

In another aspect, the systems and methods described herein include methods for predicting a patient's clinical outcomes. The methods may include collecting sample material from two or more patients along with one or more clinical outcome variables and other variables, measuring the subcellular component levels of each sample, inferring a model wherein the subcellular component levels and optionally one or more other variables are input variables and the one or more clinical outcome variables are outcome variables, inputting said patient's subcellular component levels and optionally one or more of said other variables pertaining to such patient into said model, and simulating said model to predict said clinical outcomes for said patient. In such an aspect, said subcellular component levels may be gene expression levels, protein levels or mRNA levels.

In another aspect, the systems and methods described herein include methods for identifying molecular targets for potential therapeutic intervention. The methods include simulating said model to determine which subcellular components, when increased or decreased in expression or quantity, have the most impact on said one or more clinical outcomes. In certain embodiments, said clinical outcomes are one or more of survival, recurrence, disease-free survival, effectiveness of one or more drugs, or toxicity of one or more drugs.

In still another aspect, the systems and methods described herein include methods for identifying new patients to receive one or more therapeutics. The methods include collecting sample material from two or more patients, cell lines, or animals optionally along with other variables, measuring the levels of one or more subcellular components of each sample, administering one or more therapeutics to said patient, cell lines, or animals, measuring one or more clinical outcome variables, inferring a model wherein the levels of such subcellular components and optionally one or more other variables are input variables and the one or more clinical outcome variables are outcome variables, inputting each new patient's subcellular component levels and optionally one or more of said other variables pertaining to such patient into said model, simulating said model to predict said clinical outcomes for new patient, and selecting those patients whose subcellular component levels, when input into the model and simulated, result in a prediction of one or more favorable clinical outcomes. In certain embodiments, said subcellular component levels may be gene expression levels, protein levels or mRNA levels.

In yet another aspect, the systems and methods described herein include methods for identifying new patients to receive one or more therapeutics. The methods may include collecting sample material from two or more patients, cell lines, or animals optionally along with other variables, measuring the levels of one or more subcellular components of each sample, administering one or more therapeutics to said patient, cell lines, or animals, measuring one or more clinical outcome variables, inferring a model wherein the levels of such subcellular components and optionally one or more other variables are input variables and the one or more clinical outcome variables are outcome variables, simulating said model to determine which input variables, by being either high or low, most strongly affect said one or more clinical outcomes, selecting those patients for whom said input variables are correspondingly high or low.

In another aspect, the systems and methods described herein include methods for identifying new patients to receive one or more therapeutics. The methods include collecting sample material from two or more patients along with one or more clinical outcome variables and other variables, measuring the subcellular component levels of each sample, grouping said patients into one or more patient types, inferring a patient model wherein the subcellular component levels, patient types, and optionally one or more other variables are input variables and the one or more clinical outcome variables are outcome variables, simulating a drug model to determine which subcellular component levels and other variable levels correspond to the most favorable clinical outcomes, inputting said subcellular component levels and other variable levels that correspond to the most favorable clinical outcomes into the patient model, simulating said patient model to determine which patient types correspond to the most favorable clinical outcomes.

In another aspect, the systems and methods described herein include methods identifying a new disease indication for a therapeutic. The methods may include a review of clinical variables associated with patients identified and determination of whether one or more other disease indications correspond to such clinical variables.

In another aspect, the systems and methods described herein may be used to score patients with a likelihood of placebo response. Measurements from individuals may be entered into the causal model, and a numerical value can be produced. In such an aspect, the datasets may include answers to individual questions on questionnaires, psychological scores, measurements of proteins in serum or other body parts, metabolite levels, transcriptomics, physiological measurements (HR, ECG, EEG, BP, body temperature and retinal contraction), whole genome scanning data, drug dependent responses, physical measurements (height, weight, BMI and body fat). In certain embodiments, questions that can discriminate between non-placebo responses and placebo responses may be identified. In certain embodiments, insights into physical changes that correlate with the questions can enable the development of a screening process. For e.g., a question that causes anxiety coupled with a measurement of skin temperature or heart rate.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which.

DETAILED DESCRIPTION OF THE ILLUSTRATED EMBODIMENTS

To provide an overall understanding of the invention, certain illustrative embodiments will now be described, including a system for determining and analyzing a causal model of a biological network.

The systems and methods described herein include data-driven techniques for developing causal models for biological networks. Causal network models include computational representations of the causal relationships between independent variables such as a compound of interest and dependent variables such as measured DNA alterations, changes in mRNA, protein, and metabolites to phenotypic readouts of efficacy and toxicity.

However, the embodiments set out below are merely for the purpose of illustration and it will be understood by one of ordinary skill in the art that the systems and methods described herein may be adapted and modified for other suitable applications and that such other additions and modifications will not depart from the scope hereof.

Figure 1:
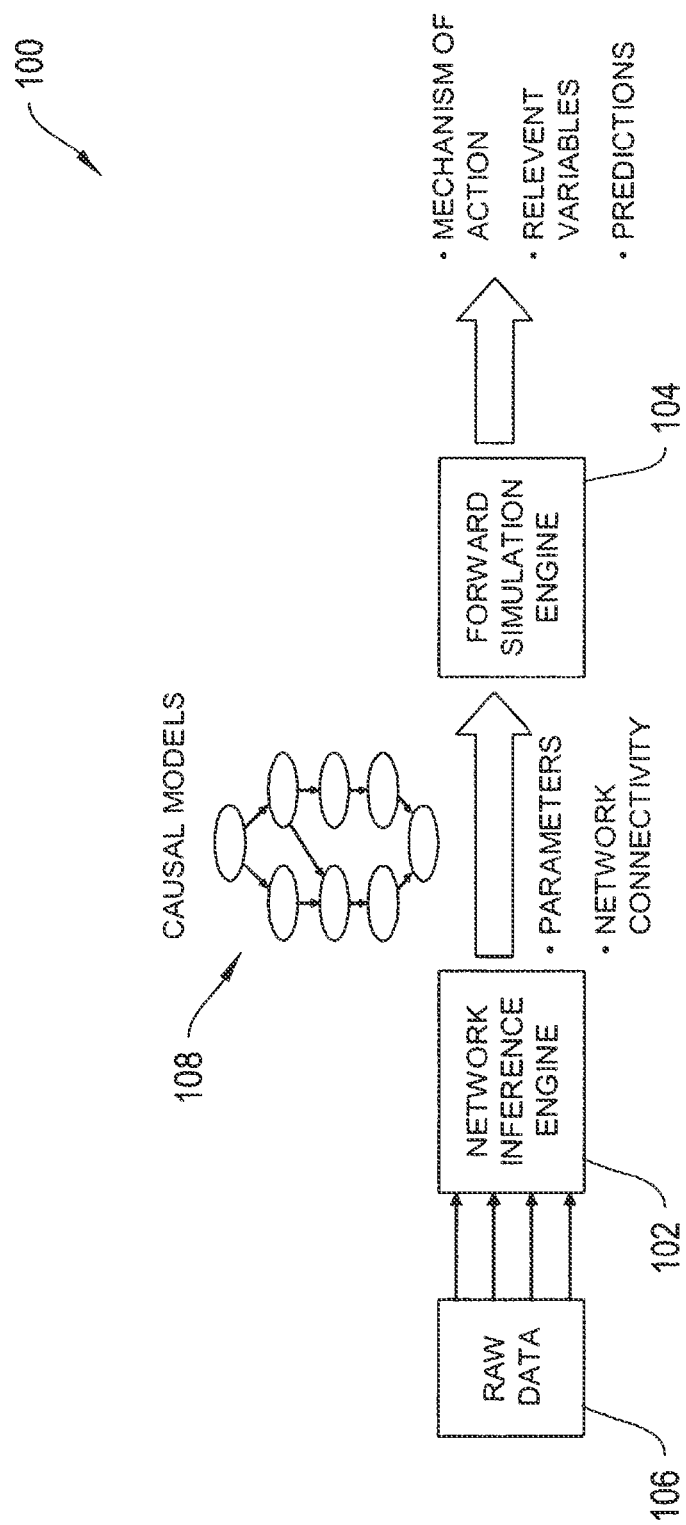
FIG. 1 is a block diagram showing a system for developing a causal model of a network, according to an illustrative embodiment of the invention.

FIG. 1 is a block diagram showing a system 100 for developing a causal model of a network from raw data, according to an illustrative embodiment of the invention. In particular, the system 100 includes a network inference (hereinafter "NI") engine 102 and a forward simulation (hereinafter "FS") engine 104. During operation, the NI engine 102 receives measured raw data 106 from one or more different sources. For example, with reference to a biological network, the raw data may include measured gene expression data showing the level of expression of a plurality of genes under certain desired conditions. As another example, with reference to a financial network, the raw data may include data describing the values of various financial measures such as prices of securities such as stocks. The raw data 106 may also include independent input data that give rise the measured data such as drug doses giving rise to a particular pattern of gene expression. The raw data 106 may further include independent output data such the efficacy or toxicity of a drug. The NI engine 102 identifies a plurality of relevant variables from the raw data 106 (e.g., gene being expressed, or stock whose price is being followed, drug or compound being studied, efficacy metric being monitored) and determines the causal relationship between these variables. The NI engine 102 develops a graphical representation of causal model 108 of the network. In certain embodiments, a graphical representation of a model is a representation that may be viewed on a computer screen, a paper printout, or some other medium, that depicts the variables in a model (e.g., with a circle or other icon), and the connections between the variables in a model (e.g., with a line or other representation of a connection).

The causal network model 108 may be depicted as a graph having one or more nodes representing the variables and the edges representing the causal relationships between the variables. The NI engine 102 determines parameters and the network connectivity for the causal relationships using the raw data 106 by applying a probabilistic search and optimization framework.

The FS engine 104 receives a plurality (or ensemble) of causal network models and attempts to identify the new values assumed by each of the variables in the causal network in response to a perturbation to one or more variables in the causal network. As an example, in a biological network for measuring the efficacy of a drug from gene expression data, the FS engine 104 may be able to determine which genes are suitable markers for the effectiveness of the therapy, by changing the values of each of the variables representing the genes in turn singly or in combination, and observing the efficacy of the drug in response to such changes. Such an understanding of the underlying causal network and the application of a focused therapy scheme may help in reducing side-effects and providing therapy primarily for patients where it may be more likely to be effective. Similarly, the genes identified as being good markers for efficacy of the drug may also be considered as targets for a second drug for combination therapy. The FS engine 104 may also be capable of simulating the model under different conditions to make predictions of the network. The FS engine 104 may be configured to interrogate and analyze a large number of models in a high-throughput manner and thereby test a large number of possible hypotheses until a robust set of causal quantitative predictions are derived.

Figure 2:
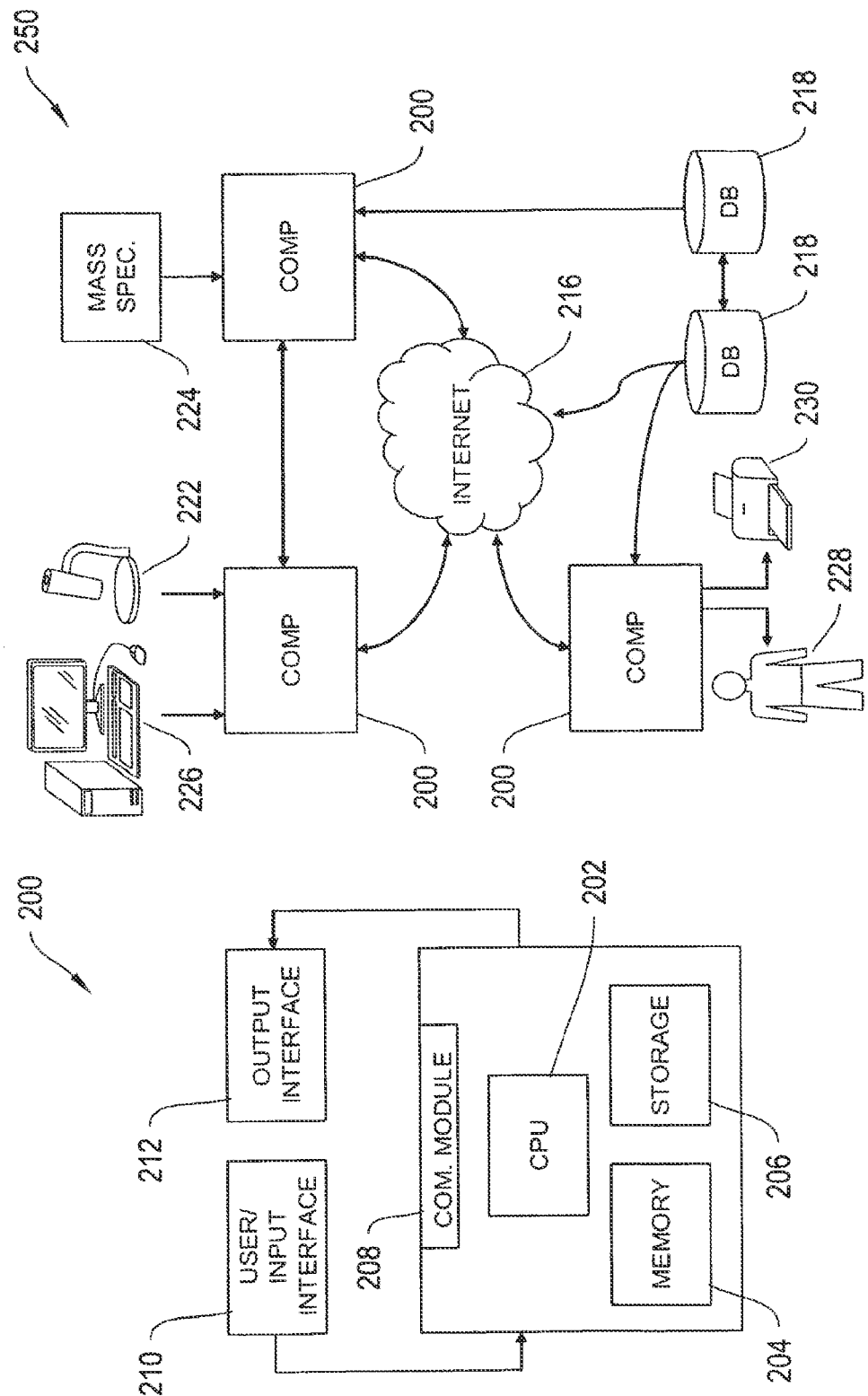
FIGS. 2A and 2B depict an illustrative computer system for implementing the system of FIG. 1.

FIG. 2A shows a functional block diagram of general purpose computer system 200 for performing the functions of the various components of system 100 depicted in FIG. 1 including the NI engine 102 and FS engine 104, according to an illustrative embodiment of the invention. The exemplary computer system 200 includes a central processing unit (CPU) 202, a memory 204, a storage 206 and a communication module 208 configured as a means for implementing one or more processes in conjunction with the system 100. The CPU 202 may include a single microprocessor or a plurality of microprocessors for configuring computer system 200 as a multi-processor system, as further described with reference to FIG. 2B. The memory 204 may include a main memory and a read only memory. The computer 200 also includes the mass storage device 206 having, for example, various disk drives, tape drives, etc. The main memory 204 also includes dynamic random access memory (DRAM) and high-speed cache memory. In operation, the main memory 204 stores at least portions of instructions and data for execution by the CPU 202.

The mass storage 206 may include one or more magnetic disk or tape drives or optical disk drives, for storing data and instructions for use by the CPU 202. At least one component of the mass storage system 206, preferably in the form of a disk drive or tape drive, stores the database used for performing various algorithms in the invention. The mass storage system 206 may also include one or more drives for various portable media, such as a floppy disk, a compact disc read only memory (CD-ROM), or an integrated circuit non-volatile memory adapter (i.e. PC-MCIA adapter) to input and output data and code to and from the computer system 200.

The computer system 200 may also include one or more input/output interfaces for communications, shown by way of example, as interface 208 for data communications via a communication network. The data interface 208 may be a modem, an Ethernet card or any other suitable data communications device. The data interface 208 may provide a relatively high-speed link to a network, such as an intranet, internet, or the Internet, either directly or through another external interface. The communication link to the network may be, for example, optical, wired, or wireless (e.g., via satellite or cellular network). Alternatively, the computer system 200 may include a mainframe or other type of host computer system capable of Web-based communications via the network.

The computer system 200 also includes suitable input/output ports 210 and 212 or use the interconnect bus for interconnection with a local display, keyboard, printer or the like serving as a local user interface for programming and/or data retrieval purposes. Alternatively, server operations personnel may interact with the system 200 for controlling and/or programming the system from remote terminal devices via the network.

The computer system 200 may run a variety of application programs and stores associated data in a database of mass storage system 206. The components contained in the computer system 200 are those typically found in general purpose computer systems used as servers, workstations, personal computers, network terminals, and the like. In fact, these components are intended to represent a broad category of such computer components that are well known in the art. Certain aspects of the invention may relate to the software elements, such as the executable code and database for the server functions of the imaging and tracking system 100.

FIG. 2B depicts an exemplary architecture of a distributed computing system 250 for performing the functions of the various components of system 100 depicted in FIG. 1 including the NI engine 102 and FS engine 104. The distributed system 250 includes a plurality of computer systems 200 of FIG. 2A interconnected either directly to each other and/or through a communication network such as the internet 216. The computer systems 200 are also connected directly and/or through the internet 216 to one or more databases 218. Raw data 106 can be received through the input/output interfaces 210 and 212 in one or more of the computer systems 200. The raw data 106 may be from other computers 226, laboratory equipment such as microscopes 222, experimental devices such as mass spectrometers 224 or human subjects 228. The output generated by the system 100 utilizing the share resources of one or more of the components of the distributed system 250 may be sent to a suitable output device such as a printer 230 or display device. The various components of system 100 may be distributed across the system 250 in any suitable manner without departing from the scope of the invention.

Figure 3:
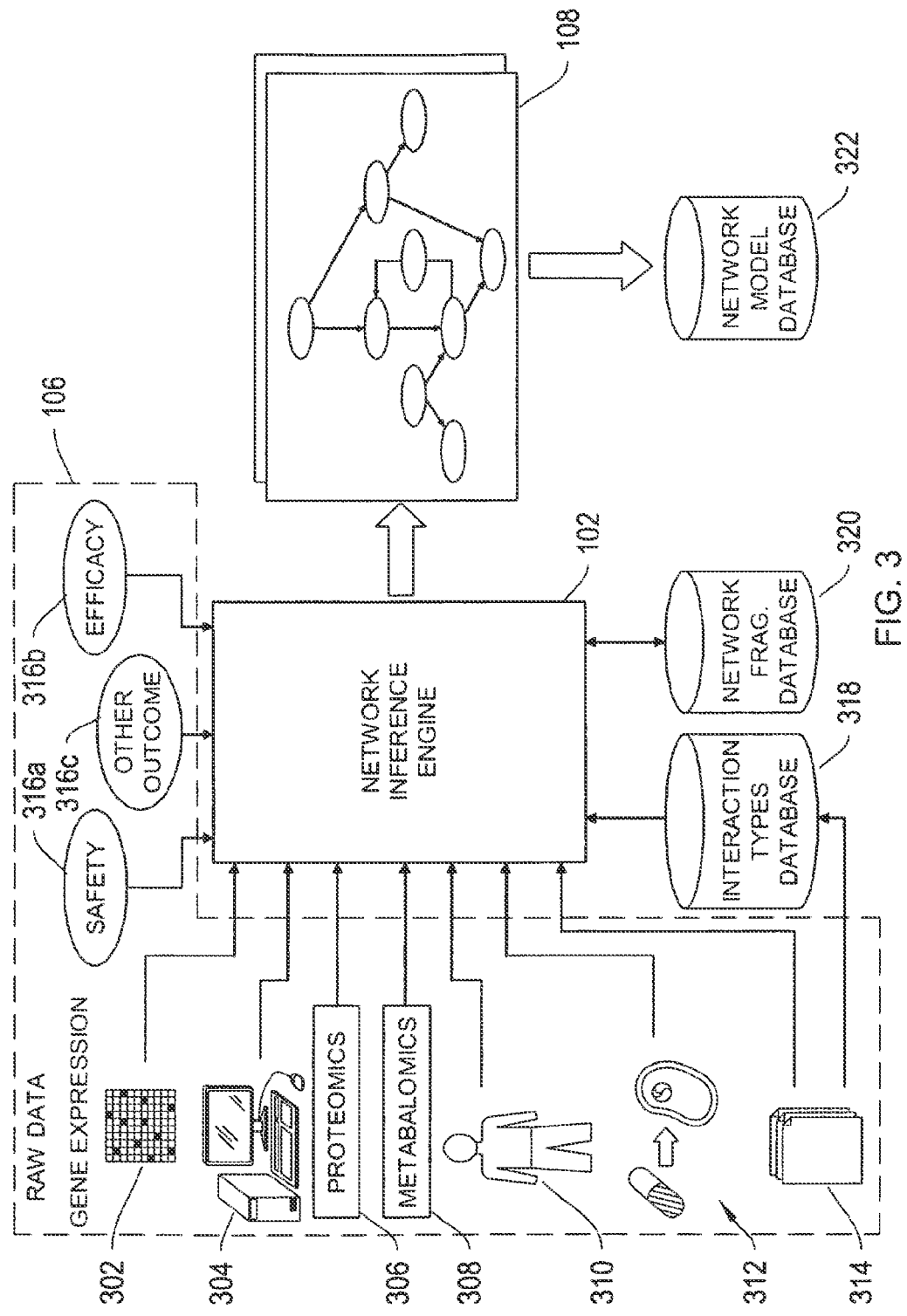
FIG. 3 depicts an exemplary network inference engine of the system of FIG. 1.

FIG. 3 depicts system 100 and particularly, NI engine 102 as applied to determine causal models for biological networks. As depicted, the NI engine 102 receives different kinds of raw data 106 from various sources. The NI engine 102 then extracts a plurality of relevant variables and determines causal relationships between them. An interaction types database 218 provides the NI engine 102 with a plurality of different mathematical functions between two or more variables. These mathematical functions can be fit to the raw data 106 to generate data-specific causal relationships. In certain embodiments, the raw data 106 may include a large quantity of data spanning many different variables and data types. In such embodiments, the NI engine 102 determines the causal relationship between some of the variables to generate network fragments. These network fragments are typically miniature causal models that may be stored in a network fragment database 320. The NI engine 102 combines the various network fragments to form an ensemble of causal network model 108 that explain the measured raw data 106. In some embodiments, these causal network models 108 are using a global optimization algorithm to assemble the network fragments contained in the network fragment database 320. These network models 108 are stored in a network model database 322 for use by the FS engine 104.

In biological networks, the raw data 106 may include inputs, measured responses and desired outcomes for clinical diagnoses and drug discovery. In certain embodiments, the raw data 106 includes high-throughput molecular profiling data 302. Such data may be obtained in gene expression microarrays, which provide snapshots of the states of one or more genes that are reflective of the biological network. The raw data 106 may include proteomic 306, metabalomic 308 and kinase assay data obtained from various cell line experiments. The raw data 106 may also include electronic medical records (EMR) 304 and updated patient specific data 310 such as age, weight and height. The raw data 106 may include other phenotypic data obtained from patients in response to drugs such as pain sensations, measurements of the quantity of molecules in the blood and sputum, and side effects. The raw data 106 may also include data from published literature including gene expressions, causal networks for particular biological systems. In one example, cultured cell lines are stimulated with measured doses of a particular compound. Cell-wide changes in mRNA expression may be measured using microarrays and thereby associate dose-dependent compound efficacy with significant changes in the mRNA levels. Genes identified may potentially be markers of drug efficacy and can be used to design low-throughput assays for improved diagnosis and monitoring drug response. In certain embodiments, the raw data 106 includes outcomes such as safety metrics 316a, efficacy metrics 316b and other outcome metrics 316c such as toxicity.

Figure 4:
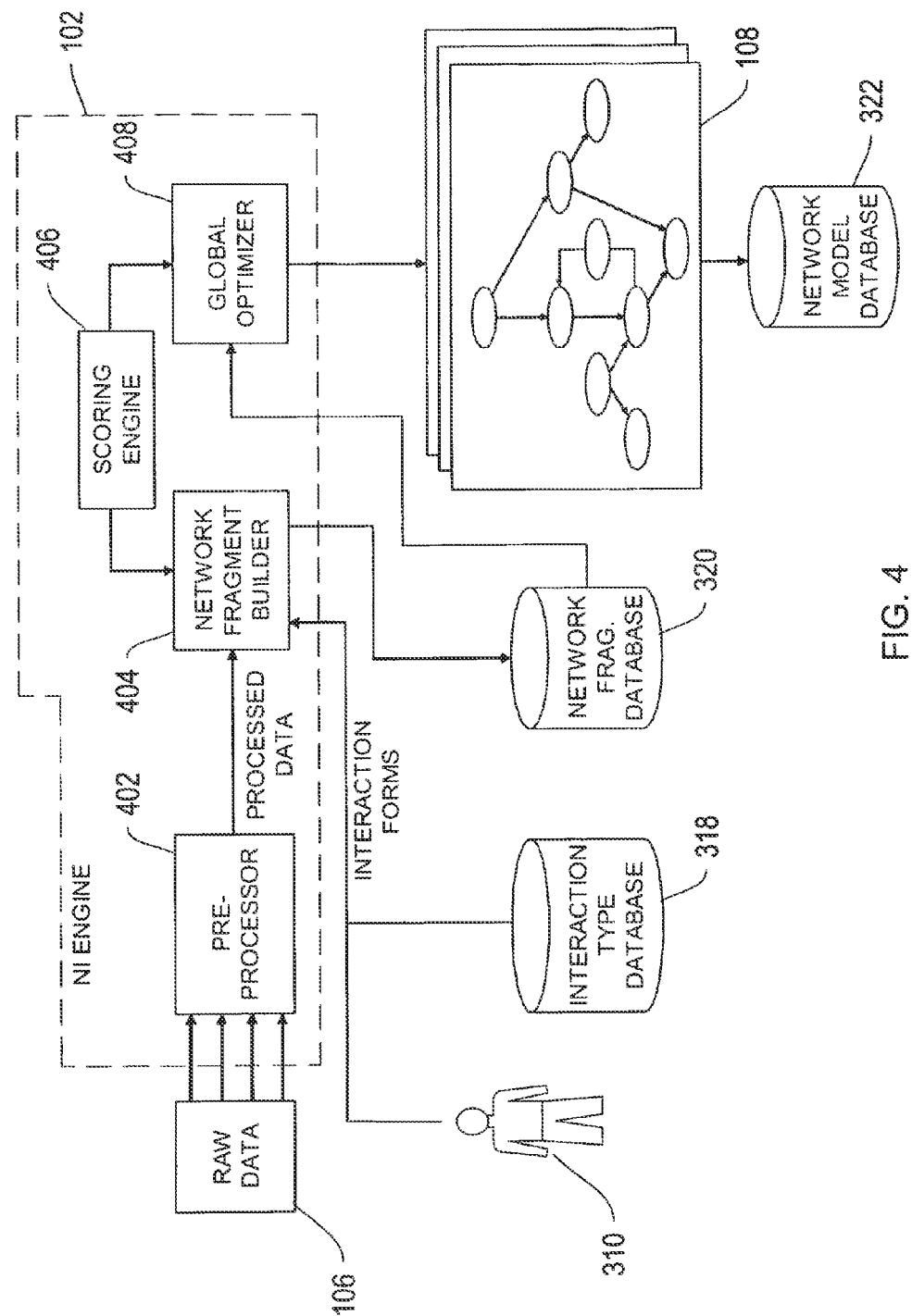
FIG. 4 depicts in more detail the network inference engine of FIG. 3, according to an illustrative embodiment of the invention.

FIG. 4 depicts, in more detail, the NI engine 102, according to an illustrative embodiment of the invention. In particular, the NI engine 102 includes a pre-processor 402 for collecting the raw data 106, a network fragment builder 404 for generating network model fragments and global optimizer 408 for aggregating the network fragments to form a causal model 108. The NI engine 102 further includes a scoring engine 406 for scoring the network fragments and causal models and thereby reducing the computational complexity of analyzing a large number of models, e.g., by eliminating low scoring network fragments, e.g., network fragments which are less likely to have given rise to the raw data 106.

The pre-processor 402 includes hardware and/or software for collecting the various types of raw data 106 and filtering out noisy measurements and those data points that may be less useful for the analysis of the network being studied. The pre-processor 402 may apply various clustering and statistical mining techniques to reduce the quantity and complexity of the raw data 106. Data quality may vary depending on the experimental technology and measurement technique. Therefore, the raw data 106 is pre-processed according to the nature of the application and received data.

In one example, data is collected from either high-throughput or high-content assays such as gene expression profiling assays. In such an example, the pre-processor 402 normalizes the sample, selects a set of expressed genes and then selects a set of differentially expressed genes. The pre-processor 402 first normalizes the sample to correct for systematic differences between samples (e.g., GeneChips). The samples in a similar treatment group are normalized followed by treatment groups in similar experiments, and then the samples are normalized by experiments. In certain embodiments, samples in a normalized data set have similar intensity values across all, or substantially all percentiles of the data. The pre-processor 402 then selects a set of genes based on their expression level as compared to a desired threshold value. Finally, the pre-processor 402 selects those genes whose maximum differential expression (ratio of the sample to the average of a pre-specified control sample group) is larger than the random difference between the samples.

Figure 5:
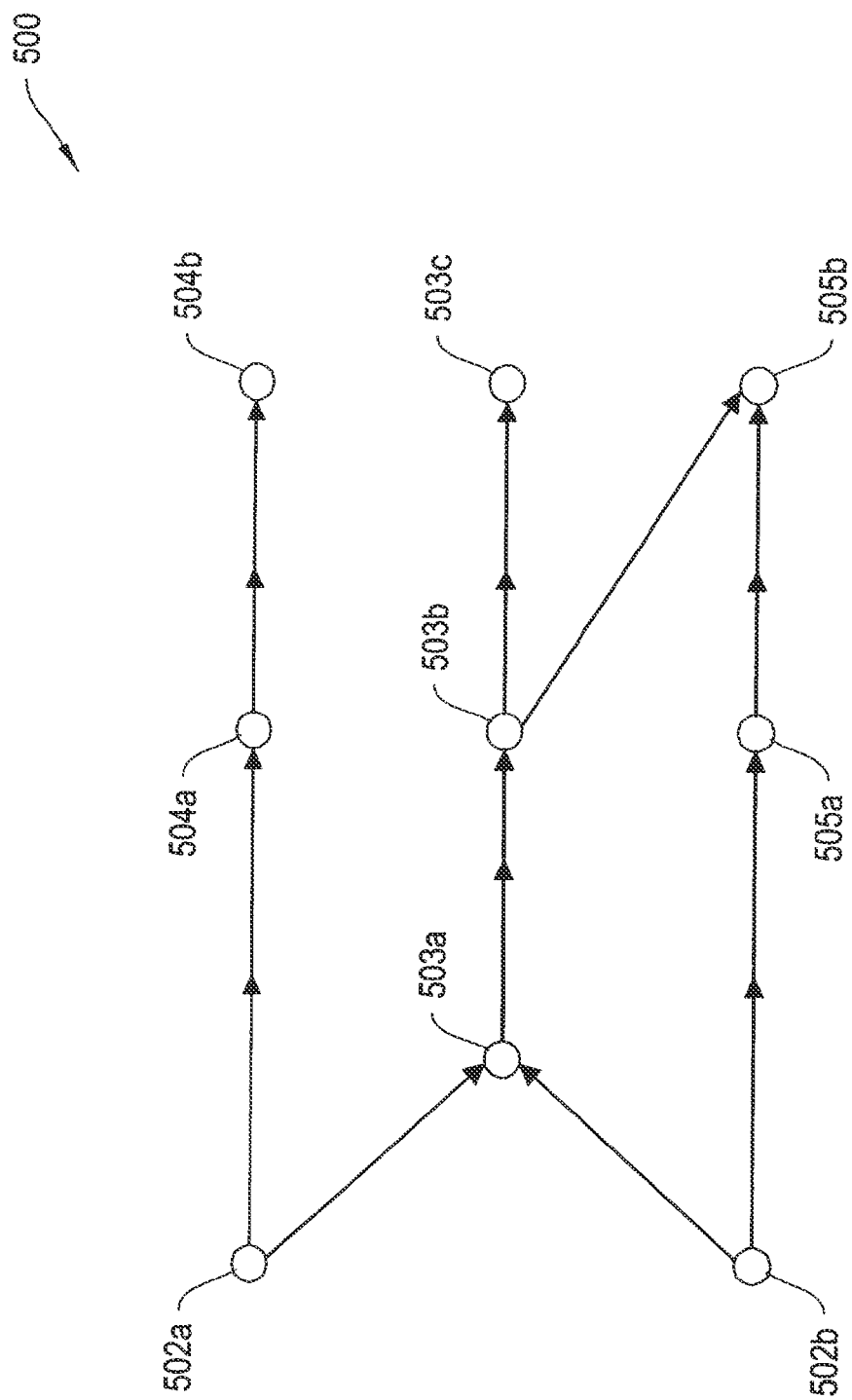
FIG. 5 depicts a graphical representation of a causal network model according to an illustrative embodiment of the invention.

The network fragment builder 404 receives the processed data including a smaller and normalized data set from the pre-processor 402. The builder 404 constructs a mathematical causal model of a fragment of the entire network using the processed data. FIG. 5 depicts a graphical representation of a causal network model 500. The model 500 depicts a biological network affected by two compounds represented by nodes 502a and 502b. Nodes 503a-505b correspond to variables or measurable entities such as gene expression levels. The model 500 describes a quantitative relationship between compounds 502a and 502b and genes 503a-505b. In certain embodiments, nodes 502a-505b are taken to correspond to log-transformed concentrations of entities. Interactions between nodes may be mediated by pathways involving proteins and transcription factors. Nodes 503b, 503b, and 505b illustrate that more than one gene may causally influence another gene.

Each edge in the graph in FIG. 5 has a quantitative relationship associated with it that describes how the expression level of a gene varies with the expression level of an upstream gene or a compound concentration. In certain embodiments, in mathematical terms, functional relationships between genes are linear functions, while relationships between compounds and genes are logistic functions, which have been found to be a common type of relationship in (log-transformed) real data. In one example, the functional relationships between the nodes in model 500 are shown below in Table 1, where a, b, c and d are parameters that are calculated based on the observed data:

TABLE 1

$$y3 = b31 + \frac{d31}{1 + \exp\left(\frac{c31 - y1}{a31}\right)} + \frac{d32}{1 + \exp\left(\frac{c32 - y2}{a32}\right)}$$

$$y4 = b43 + a43 \cdot y3$$
$$y5 = b54 + a54 \cdot y4$$

$$y6 = b61 + \frac{d61}{1 + \exp\left(\frac{c61 - y1}{a61}\right)}$$

$$y7 = b76 + a76 \cdot y6$$

$$y8 = b82 + \frac{d82}{1 + \exp\left(\frac{c82 - y2}{a82}\right)}$$

$$y9 = b98 + a98 \cdot y8$$

In the embodiment described in Table 1, y1 is the mathematical variable that represents node 502a, y2 is the mathematical variable that represents node 502b, y3 is the mathematical variable that represents 503a, y4 is the mathematical variable that represents node 503b, y5 is the mathematical variable that represents node 503c, y6 is the mathematical variable that represents node 504a, y7 is the mathematical variable that represents node 504b, y8 is the mathematical variable that represents node 505a and y9 is the mathematical variable that represents node 505b.

Returning to FIG. 4, the network fragment builder 404 generates a list of network fragments by combinatorially constructing pairs and triplets of input and output nodes. The network fragments may be stored in a database 320. These network fragments may be fit to one or more functional relationships or interaction types as described earlier. The interaction types may be fit to the processed data to estimate parameters. A researcher or user may provide a list of likely interaction types based on knowledge from published literature or the builder 404 may select an interaction type from a database 318 of interaction types. Interaction type or interaction form may mean the mathematical, logical or other interactive relationship between two variables, which may themselves be of two different types. Interaction forms may be innumerable but include linear, log-linear, sigmoidal, Boolean, switched-linear, discrete-to-discrete, discrete-to-continuous, continuous-to-discrete, continuous-to-continuous, titration curve, etc. Terms such as discrete-to-discrete may mean that one discrete variable as input leads to another discrete variable as an output.

The scoring engine 406 then scores these network fragments depending on the likelihood of the fragment representing a causal connection between the connected nodes. In certain embodiments, the scoring engine 406 operates using an underlying probabilistic framework. In such embodiments, according to such a framework, the nodes in the model 500 (measured attributes in the raw data 106 such as the expression of a gene) are represented as random variables or probability distributions whereby actual measurements of the variable represents observed values under particular experimental conditions. Applying this framework to a network having a plurality of measured attributes (e.g., genes, proteins), the system 100 represents the network as a joint probability distribution over all, or substantially all, or a plurality of random variables (e.g., probability distribution representing the expression of gene A and gene B when gene C is low). The large joint probability for an entire network may be factored into a product of local conditional probability distributions of network fragments. Such a scheme reduces the model to a product of terms, wherein each term has a few parameters. The scoring engine 406 may apply a Bayesian rule-based method to score potential network fragments. The builder 404 may prioritize the list of network fragments in the database 320 based on the score.

The global optimizer 408 may acquire a list of network fragments from the network fragment database 320 and/or from the builder 404. The optimizer 408 includes a simulated annealing sub-routine to combine network fragments and generate a causal network model. Typically, in each step of the simulated annealing process, the optimizer 408 replaces a current network model by a random fragment chosen with a probability that depends on the difference between the corresponding function values and on a global parameter called "temperature" that is gradually decreased during the process. The dependency is typically such that the current network model changes almost randomly when the temperature is large, but increasingly downhill as temperature goes to zero.

In one embodiment, the process starts at a high temperature (optimization parameter such as the average Bayesian score) with an ensemble of randomly generated networks. The ensemble is then annealed by adding and removing network fragments so that as temperature decreases, until the algorithm converges. Networks are more likely to be deleted from the ensemble (and replacement ones created) if they have a larger score. In certain embodiments, the temperature parameter has a relative scale determined by the magnitudes of scores of individual network fragments. Larger fluctuations in network score are allowed at higher temperature. The ensemble of networks at the convergence temperature represents a sample from the distribution of networks corresponding to an area in the score landscape near the global minimum. Variability of network topologies in the final ensemble may depend on the amount of data, the magnitude of noise, and the number of nodes in the network.

Convergence of the algorithm is typically verified by running optimization at least twice from different starting points. Several parameters characterizing the ensemble of networks as a function of temperature may be recorded during optimization to ensure that the run is proceeding normally and that optimization is converging. These parameters include the mean score of the ensemble of networks, the distribution of scores of networks in the ensemble and an ensemble contact map. An ensemble contact map is a summary of the ensemble in terms of its constituent edges. Convergence is achieved if the difference in these parameters between the two runs is statistically insignificant. For example, monitoring the decrease in the mean score indicates how much more likely the final ensemble explains the data relative to the initial random network.

The ensemble of causal network models 108 are stored in a database 322 from which they can be used by the FS engine 104 of system 100 in FIG. 1 for further analysis. The models 108 may be stored as a graphical representation with a tree-like structure having nodes connected by edges. The models 108 may be output and stored as a series of mathematical equations representing the causal relationship between variables. The model 108 may be output and stored as a computer script that is configured to run with the FS engine 104.

Returning to FIG. 1, the FS engine 104 may be used to extract application specific information and predictions from the ensemble of network models 108. Networks learned from data using the system 100 correspond to causal relationships in the experimental system from which the raw data was acquired where perturbations to particular variables are predicted to result in downstream changes throughout the network. A perturbation may be an influence exerted on the system that can cause a change in the system's behavior, such as a growth factor, stimulation by light or force, one or more drugs, or a genetic perturbation. A genetic perturbation may be a difference in the genetic makeup of two individuals (e.g., a single nucleotide polymorphism, or SNP), which for example may explain why one person develops cancer and another person does not. Perturbations may also generally refer to the modification of a value of a variable. The accuracy of the inferred networks can therefore be validated by, at least, readily available experimental techniques. For example, in a biological network model, the genes that appear in the neighborhood of compound nodes in the network carry the interpretation of being the genes whose change in expression in response to compound treatment is explained by the uncovered network. These genes may therefore correspond to potential biomarkers of compound activity. A biomarker may be a variable in a model that distinguishes the different types of responses of a system to a perturbation. For example, in a model built from variable representing the expression of genes, that describes the response of cancer cells to a given drug (e.g., whether the drug causes cessation or diminution of proliferation of the cancer cells), certain genes may serve as biomarkers in that the change in the level of expression of those genes are observed, upon simulating the model, to have a material impact on the degree to which the drug impacts proliferation of the cancer cells. If efficacy or toxicity endpoints are also measured then these genes in a network that connect compound to the endpoint correspond to biomarkers of drug efficacy or drug toxicity. If quantitative proteomics data (e.g., protein phosphorylation levels) are available in addition to data from cDNA microarrays, then the networks learned by including these data types in the constraining data set may uncover direct drug-protein relationships capable of elucidating compound mechanism of action at the protein level.

Figure 6A:
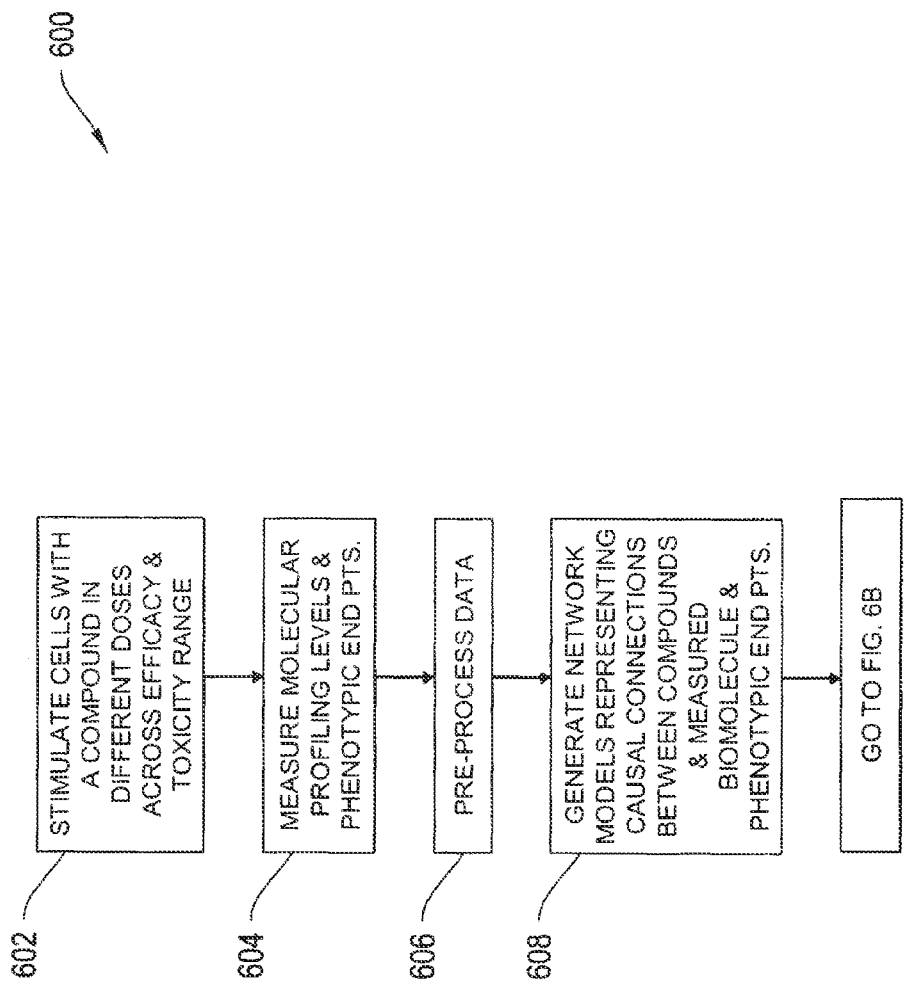
FIGS. 6A and 6B depict exemplary processes for identifying targets in a biological network for drug development.
Figure 6B:
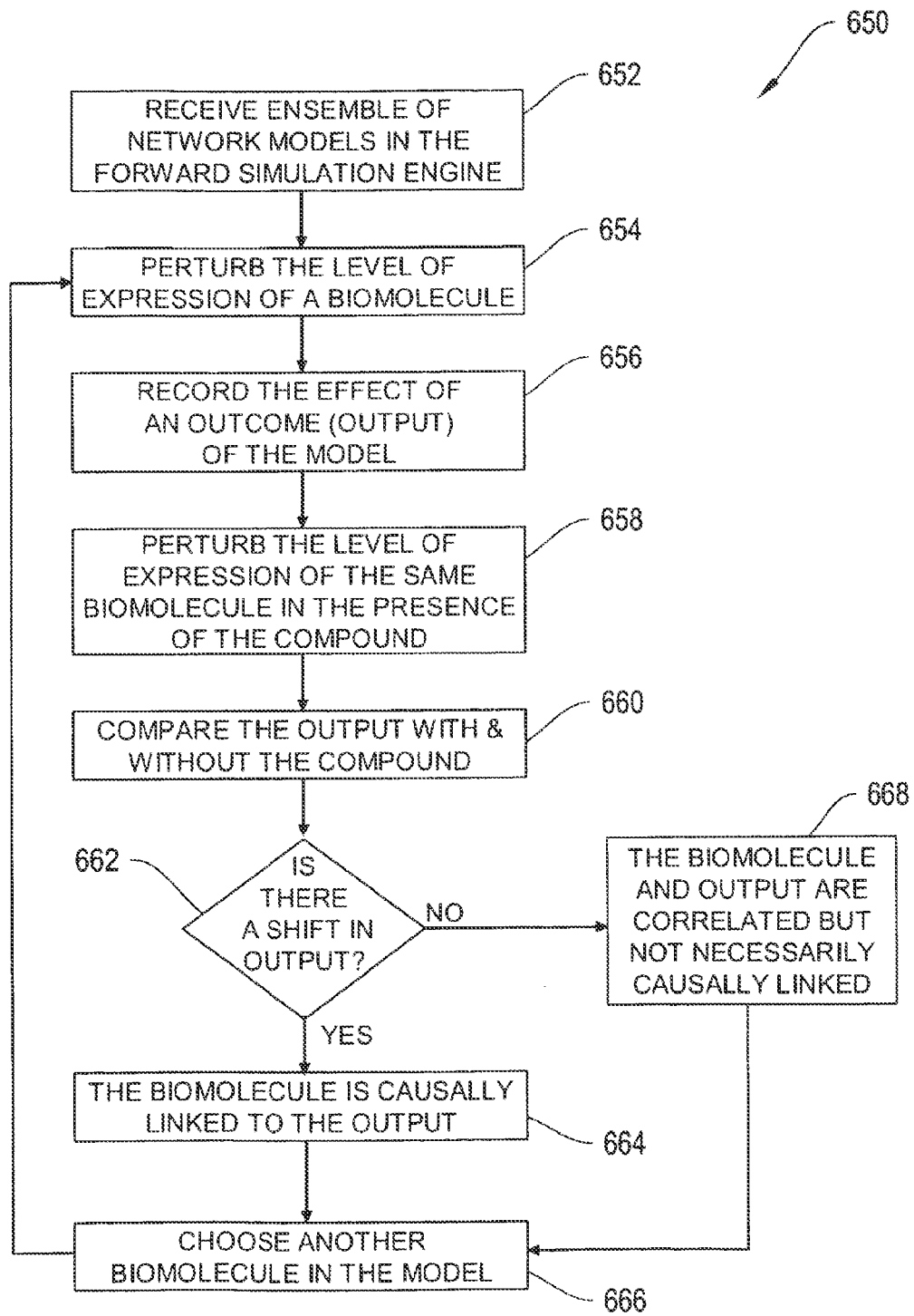

FIGS. 6A and 6B are flow diagrams depicting processes 600 and 650 for identifying targets in a biological network for drug, diagnostic or prognostic development and analysis. A target or drug target may be a biological entity which may be acted upon by a drug or other therapeutic. Because biomarkers are often part of important biochemical pathways that connect to a desired therapeutic effect, biomarkers themselves can serve as drug targets. In particular, process 600 begins with experimentally stimulating living cells with a compound of interest in different doses across a range of efficacy and toxicity values (step 602). The cell may be observed before, during and after the experiment and various molecular and phenotypic metrics may be measured, such as gene expression and cell proliferation (step 604). The raw data obtained from such measurements are sent to the NI engine 102 of system 100 depicted in FIG. 1. The pre-processor 402 (FIG. 4) collects and processes the raw data to remove noise and non-relevant data (step 606). The network fragment builder 404 (FIG. 4) and the global optimizer 408 (FIG. 4) working in conjunction with the scoring engine 406 (FIG. 4) generate an ensemble of network models representing the causal connection between the administered compound and measured biomolecule and phenotypic end points such as gene levels, efficacy and toxicity (step 608).

The NI engine 102 sends this ensemble of models to the FS engine 104. The FS engine 104 performs a process 650 for analyzing the models and identifying suitable biomarkers. The process begins with receiving the ensemble of network models from the NI engine 102 or a network model database 322 (FIG. 3) (step 652). The FS engine 104 artificially (computationally) perturbs the concentration of one or more drugs contained in the network models (step 654). biomolecules represented by one or more nodes in the network (step 654). The FS engine 104 may record the effect of the perturbation on the outcome or outcomes of the model (e.g., efficacy or toxicity) (step 656).

The FS engine 104 also perturbs the same concentration of one or more drugs contained in the network models while perturbing the expression level of a gene represented by a node. Since the networks are typically causal networks, a change in one node may impact many other nodes in the network. The FS engine 104 records the effect of the perturbation of the gene node and drug node at the same time on the outcome or outcomes of the model (e.g., efficacy or toxicity) (step 658). The FS engine 104 then compares the output with and without the compound for one or more of the models in the ensemble of models. In certain embodiments, if there is a shift in the output (step 662), the FS engine 104 may conclude that the biomolecule under consideration is directly causally linked to the output and may be a suitable target for further testing (step 664). If there is minimal or little shift in the output, then the biomolecule and the output may be correlated but not necessarily causally linked (step 668). The FS engine 104 then selects another biomolecule(s) for review and performs the process 650 again. In certain embodiments the FS engine 104 extracts the genetics-dependent mechanism of efficacy, mechanism of toxicity, or biomarkers of efficacy or toxicity with respect to the use of one or more drugs in the biological system. A biological response to a drug may be genetics dependent, in that one or more variations (e.g., SNPs) in the genetic makeup between two biological entities of the same species can cause the two entities to exhibit different responses to the same perturbation.

The network inference/reverse engineering techniques can be used in concert with other bioinformatics tools known to one of skill in the art, as well as bioinformatics tools embodied in patents and patent applications commonly owned with this patent application and incorporated by reference. It should be appreciated that diverse data types (e.g., molecular, phenotypic, etc.) can be used as inputs to the reverse engineered models, which increases the degree of robustness of the resultant biological system models according to certain embodiments. Further, it should be appreciated that the network inference methods disclosed herein can be applied to the development of a wide range of therapies, including but not limited to small molecules, biologics, aptomers, RNAi, etc., because the methods are agnostic to the type of data being analyzed.

In addition to the uses detailed above, the systems and methods described herein may be used in concert with any technology known to one of skill in the art for designing target-specific therapies. For example, the systems and methods may be used to identify drug targets for cancer therapies on a patient-specific basis, and utilizing existing siRNA and shRNA design technology to specifically "hit" the identified targets.

The examples set forth herein are intended to be illustrative and not limiting. One skilled in the art can conceive of several other applications of the systems and methods described as set forth herein. For example, a problem facing one skilled in the art is the use of multiple drugs together in a therapeutic combination, in which the synergistic effects of the combination are postulated but unknown and the toxicity of such a combination are unknown. The system enables a rapid screening of several combinations of two, three or more available drugs in various cell lines or by other methods known to one of skill in the art and analyzing the resulting data, either before or after additional bioinformatics processing, using the network inference methods taught herein, and enabling an understanding of how the combination therapy affects the Networks within such cell lines and actually changes the cell biology, and what toxicities emerge from the use of such combinations.

One skilled in the art might also utilize the present invention to validate previous assertions about the existing components of a biological system; this application might be particularly useful in areas where experimental measurements giving rise to such assertions are unusually prone to error. One skilled in the art might use the methods to conduct image analysis on either biological or other systems; for example, certain datasets might contain only images of a system to be analyzed, such as a set of pictures of microphages. The change in morphology of the microphages might be analyzed solely by a set of image-related variables, including but not limited to color intensity, fractal dimension and lacunarity. Alternatively, the image analysis can be merged with the types of data discussed earlier in this document (genetic and cell biology data measured by microarrays and other methods). This latter point may be an important point to recognize about the present invention; the invention may be agnostic about the types of data to be analyzed. Data from image analysis, genetic analysis, outcomes analysis (e.g., a binary result of tumor death or not, or tumor progression or not), can all be integrated and processed to determine the underlying causal connections between the variables using the methods of the present invention.

In one embodiment, the present invention can be used to discover biomarkers and targets for therapeutics from clinical data from patients, using a process along the lines of the following:

Step 1—Collect datasets that measure particular biological measurements of interest to serve as causal molecular drives of disease and or drug mechanism of action (including but not limited to: gene expression levels from a DNA microarray, RT-PCR, or other methods known to one of skill in the art; proteomics data from 2-D GELs or from other measurement methods known to one of skill in the art; single nucleotide polymorphisms (SNPs) measured by using a "SNP-chip" on a blood sample or some other measurement of SNPs known to one of skill in the art; metabolomics measurements—the quantity of any of a number of molecules in blood, urine, sputum, etc.; or any other biological measurement known to one of skill in the art) and one or more outcomes of interest as an output variable. In the remainder of the explanation, molecular profiling data from patient biopsies will represent molecular nodes (e.g. genes, proteins, metabolites) that can causally impact clinical physiological outcomes (e.g. tumor response to treatment, survival time post operative surgery, etc.) which we will refer to as clinical outcome node. In addition, molecular nodes can be driven by independent clinical features that differentiate between patient subgroups such as tumor grade or other fine/gross clinical features (e.g. Her2+ vs. Her2− patients). It is reiterated that any molecular nodes and clinical outcome nodes representing biological entities and outcomes known to one of skill in the art may be used in place of the below specific example (e.g., in a metabolic disease application, proteomics data from 2-D GELS might be the input nodes and the output nodes might be level of insulin resistance and/or degree of beta cell functionality).

From molecular profiling data, clinical response measurements, and clinical features of a population of patients models can be reverse engineered that causally link molecular nodes to clinical outcome nodes. In addition, it should be possible to include features such as different patient subgroups that drive molecular nodes and their impact on clinical outcomes. These drives act as independent input nodes.

The collection of genotyping data including SNPs, methylation patterns, RFLPs, micro-satellite markers and copy-number polymorphisms allows the identification of causal anchors from which biological causal networks can be connected through high-throughput molecular phenotypes (including gene expression, proteomics and metabolic measures) to traditional clinical measurements of disease. The networks derived from the integration of these data-types are causal because they represent the central dogma of biology that DNA variations drive phenotypic variation and ultimately clinical outcomes under particular environmental conditions. Simulation of the networks can lead to genetic insights related to epistasis and complex, multi-gene traits that are otherwise difficult to uncover.

Step 2—Use the methods of the present invention to reverse-engineer a model (the "REFS Model") containing, for example, gene expression data (molecular nodes) and survival outcome (clinical outcome node) from a population of patients with a cancer type of interest.

Step 3—Use the methods of the present invention to systematically perturb each of the molecular nodes (genes) in the REFS Model. This can be achieved by setting the levels of expression of genes up or down by a large amount as compared to its level in the REFS Model right after it is created by reverse-engineering (the "Original REFS Model"). In one embodiment, this would be achieved by a ten-fold "knockdown" (reduction) in gene expression of each gene (input node), one at a time, and a ten-fold "overexpression" (increase) in gene expression of each gene, one at a time. The genes that most affect the endpoint(s) of interest (in this example, survival), can be identified. Given more time and/or computational resources, multiple and combinations of genes can be overexpressed up and/or knocked down at various levels simultaneously to observe cumulative impact of these actions on the endpoint(s) of interest.

Step 4—From the genes identified as having the most impact on the endpoint(s) of interest, identify the variability of those genes from the clinical data set. Here one can use data from larger population studies to determine human variation in molecular profiling expressions. For example, ten genes might be identified as the most impactful on survival in the cancer example. Note, importantly, that the genes that move the endpoint the most when knocked up or knocked down ten-fold, may not have as much natural variation in the clinical data set. For example, Gene X may cause an increase in survival from 100 days to 300 days when it is knocked down ten fold. However, it may be that the variation in Gene X in a given patient is only between a level of 5 and 6, and appears in the Original REFS Model at a level of 5.5. Meanwhile, Gene Y may cause an increase in survival from 100 days to 200 days when it is knocked down ten fold, but Gene Y varies across the clinical data set in amounts from 1 to 21, and occurs in the Original REFS model at a level of 10, such that it would be possible to find at least one patient for whom we could actually observe the equivalent of a knock down Gene Y by a factor of 10 ($^{10}/_{10}$=1), and thus expect survival to increase from 100 to 200 days. Meanwhile (assuming a linear relationship between these variables for purposes of simplicity in the example), we can only observe a knockdown of Gene X from 5.5 to 5 (a knockdown of a factor of 0.5/5.5=0.09, or approximately 0.1-fold), so that we might only expect survival to increase by 0.1-fold/10 fold or $^{1}/_{100}$ of the total increase in survival of 300-100=200, or a total increase of only two days). Thus, the "in silico" knockdown/up of Step 3 is not enough; the natural human variability is important to observe.

Step 5—Return to the REFS Model and cause a variation of those genes within the limits of the naturally occurring variation in the clinical dataset (testing out single and combinations of gene variation). For example, Gene X may have shown a level of expression of 3-7 across the 150 patients in a clinical dataset that the methods of the invention were applied to in order to obtain the REFS Model. Gene X would then be set to 3 in the Original REFS Model, the Original REFS Model would be forward simulated, and the survival output node would be observed—for example, the survival output node might result in a survival of 120 days. Gene X would then be set to 7 in the Original REFS Model, the Original REFS Model would be forward simulated, and the survival output node would be observed—for example, the survival output node might result in a survival of 70 days. This would be repeated for all genes identified in Step 3.

The exact nature of the simulations performed in steps 3 and 4 will also depend on the type of model generated as discussed above. For example, in a model where the different tumor stages act as input nodes that causally drive molecular nodes, these will be given different setting to arrive at genes that effect survival time between different tumor stages.

These results can also be derived by employing a Bayesian Belief propagator (rather than the forward simulation step described herein) to determine what are the molecular factors that lead to an increase or decrease in survival time.

The result of this process is a set of biomarkers (the identified genes) that shift the output node of interest/endpoint and whose variation in humans is enough to shift the endpoint. To assess the significance of the biomarkers chosen a scoring function which seeks to mathematically combine simulation results that suggest what magnitude of change in the marker is important with information pertaining to a particular detection system to accurately report on the simulation-derived changes in a clinical setting.

The present invention also involves methods of using the same process as set forth in the above-enumerated steps to predict the success of clinical trials and/or to properly populate clinical trials. A clinical trial data set is analyzed using the above steps to gain an understanding of the limits of human variability in genes (molecular nodes) that are identified to be causal drives of survival (clinical outcome nodes).

If a given drug is known to impact a certain gene, the REFS Models created by Steps 1-5 may be used to test how that drug would impact clinical outcome "in silico" and determine a set of biomarkers (the identified genes) that shift the output node of interest/endpoint and whose observed variation in humans is enough to shift the endpoint. Once this is learned from one phase of a trial (say a Phase I or II), one can use the predicted models, biomarkers, and data on human variation of these genes to determine the success of the next phase of a clinical trial (say from a Phase I to II or Phase II to III). In particular, one can assess the success of the trial if patients are chosen randomly versus if they are selected based on the variation in one or more or any combination of the discovered biomarkers using data on how they vary in a larger population. For example, the success rate of a clinical trial might be predicted at 10% if no biomarkers are used to pre-select patients for the next phase, to 25% if one of the most highly ranked biomarkers is observed, to 50% if two of the markers are used to pre-select patients, to say only 53% if three of the relevant biomarkers are used to pre-select patients. In this case, one would conclude that there are economic benefits of measuring two markers to pre-select patients despite the fact that it would cost more, but not much benefit to measuring three. Similar computational analysis can be done once a treatment is approved to do a cost benefit analysis of a companion biomarker that would accompany a treatment based on a Phase III and IV clinical trial. And similarly again, such an analysis can be conducted on drugs that are already approved from prospective therapeutic studies.

[New Section] The present invention can be used to tie genomic information to clinical data to discover biomarkers, identify targets for disease prognosis, and identify therapeutic options for patients, as follows:

Step 1—Collect genotyping data on the appropriate biological samples. These should exhibit the appropriate variation in phenotypes underlying the biological process of interest: variations in disease patho-physiology and or response to therapies of interest. Genotyping measurements can include (but is not limited to): single-nucleotide polymorphisms, genomic copy number polymorphisms, epigenetic status (e.g. methylation, aceytlation, . . . ), full genome sequencing, and micro-satellite markers.

Step 2—Collect clinical phenotypic data on organisms consisting of disease patho-physiology, response to therapy, and or response to biological factors/processes of interest.

In addition, collect any clinical information relevant for the biological process of interest such as weight, blood pressure, diagnosis and treatment history, race, gender, etc. Additional clinical information can include inheritance structure of the human population in the study (possible in inbred sub-populations such as those found in Iceland). This information can help separate out causal genetic features from normal variations seen in the normal human population. This can be incorporated into step 4 to determine genetic features around which to build the models.

Step 3—Collect any additional clinical molecular data indicative of disease phenotype and or response to therapy including blood and urine biomarkers, clinical chemistry measurements, and pathology scores.

Step 4—One can run computational analysis (e.g. linear modeling, mutual information analysis . . . etc.) to determine (statistically) significant genetic features associated with phenotypes of interest and other clinical data described in Steps 2 and 3. This can be run for single as well as pair-wise, triplet, . . . etc. sets of genetic features (e.g. pair-wise SNPs that drive phenotypic response). The output from this analysis can serve as input into the reverse-engineering and simulation process of the invention—list of (statistically) significant genetic features, phenotypes, and other associated clinical data.

In addition, computational analysis can be run to determine if clinical information such as gender, race, strain etc. effects phenotypic response. This can be used to appropriately determine which relationships to model and or ways of segregating the patient population into appropriate training groups.

Prior to running the reverse engineering engine one can employ another step in the analysis that would include discretizing the data set to appropriately couple discrete genomic data with continuous data types from additional clinical data.

Step 5—Run the reverse-engineering method of the invention to determine the ensemble of models/networks capturing the relationships between genotypes, phenotypes, and other associated clinical data.

To address the issue of epistasis from these data sets, the interaction of two or more genes that can modify an organism's phenotype, the present invention proposes using priors. Typically the genes assort independently but can often be found associated with a particular phenotype and appear to be strongly linked. Statistical analysis of epistatic genes may provide better evidence for disease associated groups of genes than by analyzing the genes singly. However, due to SNP frequencies in the population and cost constraints, it might not be feasible or desirable to survey enough genetic samples to have all combinations of gene variants in the data set. Further, epigenetic modification and copy number polymorphism at genetic loci can increase the numbers of combinations. This causes problems for statistical analysis for epistasis as current methods require enumeration and address this limitation with several approaches. Here we use prior information about the expected distribution of SNPs in the organism population to be used in the calculations. This allows individual, reasoned approximations to be calculated for each epistatic combination and further allows for meaningful forward simulation of in silico genotyping experiments that have a meaningful, data driven basis.

Step 6—Run the forward simulation engine to determine one or more of the following:

1. Predictions of prognosis and or therapeutic response— each node in the model can be set to reflect a patient's genotypic measurement and other clinical measurements from the patient's sample (e.g. tissue, blood, urine, . . . etc. biopsies) and used to predict outcome of disease phenotype and or therapeutic response.

2. Predictions of markers for diagnostics and or therapeutic interventions: perturb each of the genetic features (e.g. in silico knockout/knockin of the genetic feature and or clinical markers in the model (which if continuous one can knock-down or unregulated)) in the model singly and in combination to determine which of the genes causally influence phenotypic outcomes and other clinically relevant variables.

In the case of applying these models to predict response to therapy, these models can be used to help in clinical trial design and optimization. For example, models determined from Phase I clinical response data using Steps 1-6 can be used to predict toxicity markers that can be used to monitor patients in subsequence trials and determine optimal dosing. Models developed from data in a Phase II or III trial can be used to select patients for a larger Phase III study or used to develop a diagnostic to determine which patients to apply the drug to (see previous provisional patents to determine methods of application in clinical trials and post marketing of the drug for models generated from clinical data).

The present invention can be used to address toxicity concerns and issues in biological systems and related drug development, such as identification of causal relationships of biomolecules, small molecules including metabolites to a drug safety issue such as phospholipidosis, cholestasis, steatosis, nephrotoxicity, pulmonary toxicity, immunotoxicity, reproductive toxicity, genotoxicity, cardiotoxicity, osteotoxicity, neurotoxicity, dermatologic reaction or other safety issue of concern to drug safety or military personnel safety using proteomic, GeneChip, metabalomic data sets combined with a clinical endpoint such as a morphometry measurement, EnzymeLinked ImmunoSorbent Assay (ELISA) that is used as an assay for drug or environmental safety testing. The identification of the biomolecule or small molecule would enable the development of an assay to detect the response in humans.

As previously addressed, the systems and methods described herein may be used in combination therapy development. In one embodiment, the use of a small library of well defined chemical or physical (such as heat, radiation with electromagnetic fields or waves) test in a defined sequence to enable the prediction of the causal network of biomolecules necessary for a drug response or drug side effect/safety issue using either tissue culture, primary cells, 3D cultured cells, xenografts, animals, stem cells, morphologically differentiated or patterned cells as the test media, and GenenChip, metabalomic, proteomic, lipomic, glycomic or other large scale surveying technology to provide a physical readout from the assay.

One skilled in the computational arts will appreciate that the same methods set forth in the current invention may be utilized in the determination of the structure, connectivity, and causal relationships between nodes, for networks other than biological networks. In addition, any sort of qualitative data, by being converted into numerical data (e.g., a customer rates their experience from 1-5, where 1 is very bad and 5 is very good), can be utilized as a variable in the networks that are inferred. In addition, non-numerical data (e.g., Boolean or discrete states) can be utilized within the invention. The systems described herein can serve as a knowledge integration tool generally due to its flexibility in the types of data that can be combined within it.

For example, the reverse-engineering and forward simulation described herein has been used in quantitative finance applications to make predictions about future prices and returns of various securities. For example, twelve years' worth of data were assembled regarding the previous prices of natural gas futures contracts, along with other data describing the demand, supply, and holdings of such contracts, over a period of several years. Variables included each of the prices and various summary statistic variables and time lag variables (e.g., the moving average of a variable over the previous year, or the value of a variable one week, one month or one year in the past). Using the invention, models were built and displayed in graphical form that reflected the connections between the variables and the endpoint, or output variable, of interest (in this case, the one week forward price of a natural gas futures contract). According to the principles of the invention, these graphical models contained edges that were represented by underlying equations showing the relationship between the variables connected by the edges. Therefore, these graphical models could be simulated to make predictions about the output variable, given a set of input variables. The models were tested on the subsequent year (an "out of sample" test) to determine the accuracy with which the models predicted the directionality of one-week forward price changes (e.g., up or down) of natural gas futures contracts, e.g., on data that was not used to build the models. This test yielded an initial result of 79% accuracy for one-week predictions over the test year.

Importantly, in certain embodiments of the invention, the data modeled and simulated using the current invention may include time series data, such that, e.g., given a set of variables A-J and times 1-10 (noted as A1-J10), the invention may be used to construct models that show how variable A1 causally influences variable F3, even though A1 may not be observed to causally and materially influence variable F2 or F4. It may be that variable F is not typically reported at time 3, but is an important variable to have an estimated value for in order to make a decision, or to input into another node in the model to make a prediction at time 3. The invention may also be used to do rapid feature selection, e.g., which of variables A1-I10 and J1-J9 are best predictors of variable J10.

The invention may be of particular utility in creating a cross-markets model, in which, e.g., variables measuring certain market indices or other proxies for market performance are measured over time and used as raw data. The invention would then enable the construction and simulation of models that would predict the future value of one or more indices. For example, there may be a series of data on market indices collected that include energy indices and transportation indices. Models built using the current invention on the market indices may predict that given the simulated change in value of an energy index at time zero, the value of an energy index at time t is expected to go down by a certain amount, with a certain probability.

The commercial value of insights into the causal relationships between various financial variables may be significant; for example, financial investors could make informed investment decisions based on the understanding that a change in certain financial variables will likely result in a positive or adverse effect on the price of a certain security that the investors are considering for purchase.

Similarly, certain aspects of the present invention may be used with internet search engines seeking to understand ways in which to increase revenues associated with each search (e.g., by identifying causal connections between the methods determining which advertisements are displayed alongside search results and resulting advertisement revenue, by helping to maximize "dollars per click", etc.). The data available to conduct such analyses might include data regarding the people viewing each webpage (e.g., type of computer being used to view the page, is the user male or female, user's age, user's income, previous pages viewed by user, previous views of different parts of webpages, previous purchases from different online sites, etc.). The present invention would then be utilized to observe the causal connections between the aforementioned variables and the user's subsequent behavior (e.g., what will the user click on next, what is the best content or advertising to display to the user next to maximize likelihood of advertising revenue, etc.).

The relationships forming the basis for human thought processes and the systems underlying such processes might be inferred using the methods of the present invention. On a broader scale, the evaluation of social networks may be conducted using the present invention; for example, to determine the proper allocation of resources in a community, simple statistical analyses are currently used in some cases to determine how to make either or decisions between choices such as increasing teacher salaries, decreasing class size, increasing the number of policemen, or spending more money on keeping public areas and public transportation clean and pleasant. Causality may be critical to understanding social networks and properly effecting change in such networks. The systems and methods described herein may be used to address the long-standing inability of existing methods to discern the latent causal relationships between variables in a community budget, and is designed in such a way as to be commercially implemented in a software product to address questions of social networks. Similarly, the systems and methods may be used as a tool for decision-makers in a corporate entity, who have at their disposal a wide array of data about sales, productivity, activities in the marketplace, activities of competitors, customer behavior, etc., and need to make decisions based on these data, but do not have a full appreciation of the causal connection between the variables. For these decision-makers, the systems described herein can serve as a prognosticator. First, the input data would be used to infer the causal connections between the variables. Second, a model that can be forward-simulated, just as for biological applications as noted above, could be created, and the decision-maker could play out various scenarios to understand the results of his or her actions.

Because the systems and methods may be capable of drawing out probable causal connections between variables in a dataset, they may be very useful as a front-end to simulation software. Simulations built using the systems are extremely robust in their incorporation of causality. Such simulations might be used by sports team owners to play out full simulated seasons with different players, incorporating salaries as well as player performance and game outcome statistics, to determine the optimum team to assemble and the maximum amounts, with myriad variables taken into consideration, from the likelihood of a certain type of player to get hurt to the historical performance of a player or team. Such simulations might also be used to create realistic video games that mimic actual live sporting events, because the causal connections that drive the results in the real games would be incorporated into the game simulation software. Similarly, the social network analysis noted above in conjunction with the systems and methods described herein might give rise to a much more realistic version of video games such as SimCity.

The present invention might also be embodied in a software tool for customer service applications. Customer experience may be rendered quantitative using the conversion method described briefly above, and the interactions between the many variables in, for example, airline service (percentage flights on time, percentage baggage lost, wait times in ticket lines, etc), and help airlines improve customer service (or more broadly, to determine that efforts in customer service and/or advertising quality of customer service are not cost-effective). One of the advantages of the systems and methods described herein is that it is particularly useful in drawing out causal connections between several large datasets, as it can be implemented in a high-throughput manner without a lot of costly human/manual intervention.

As previously stated, the foregoing examples are not intended to limit the scope of the applications of the present invention; the invention might be applied to any network comprised of nodes/variables in which the interactions and causality between the nodes is partially or completely unknown, for which data, whether quantitative or qualitative describing the nodes is available to help build the initial models, and the result in each case is a deeper, data-driven understanding of the causal relationships between the nodes/variables.

The present invention may also be used to develop an understanding of when a model of a system is becoming a less valid descriptor of the underlying system. For example, a set of nodes to be turned into a model is comprised of variables A1 through J10, where numbers 1 through 10 represent time steps 1 through 10. Variables A through J are observed over one hundred time steps, where variable J is the output variable of interest. Twenty-one models are built (e.g., one model for times 1-10, another for times 2-11, etc.) on the time points 1 through 20. Then, the twenty-one models are tested on the data after time 20. The accuracy of the models in predicting the subsequent values (e.g., how well does the model trained on times 1-10 predict J11, how well does the model trained on times 2-11 predict J12, etc.). The accuracy of each model in predicting the next time is observed, and the value of each of the other variables A-I is noted when each new prediction is made. If any one or more of variables A-J tend to be far out of their normal range in the next series of data (e.g., for the model trained on times 2-11, variable F12 is far outside of its normal range, and the resulting prediction for J12 is poor), and if these variables consistently appear as being out of their normal range (e.g., variable F), these variables may be said to be predictive of when the model will fail and when a new model must be constructed.

It will be apparent to those of ordinary skill in the art that methods involved in the present invention as well as the means for implementing the methods described herein may be embodied in a computer program product that includes a computer usable and/or readable medium similar to computer system 200 (FIGS. 2A and 2B). For example, such a computer usable medium may consist of a read only memory device, such as a CD ROM disk or conventional ROM devices, or a random access memory, such as a hard drive device or a computer diskette, having a computer readable program code stored thereon.

The process described herein may be executed on a conventional data processing platform such as an IBM PC-compatible computer running the Windows operating systems, a SUN workstation running a UNIX operating system or another equivalent personal computer or workstation. Alternatively, the data processing system may comprise a dedicated processing system that includes an embedded programmable data processing unit. For example, the data processing system may comprise a single board computer system that has been integrated into a system for performing micro-array analysis.

The process described herein may also be realized as a software component operating on a conventional data processing system such as a UNIX workstation. In such an embodiment, the process may be implemented as a computer program written in any of several languages well-known to those of ordinary skill in the art, such as (but not limited to) C, C++, FORTRAN, Java or BASIC. The process may also be executed on commonly available clusters of processors, such as Western Scientific Linux clusters, which are able to allow parallel execution of all or some of the steps in the present process.

As noted above, the order in which the steps of the present method are performed is purely illustrative in nature. In fact, the steps can be performed in any order or in parallel, unless otherwise indicated by the present disclosure.

The method of the present invention may be performed in either hardware, software, or any combination thereof, as those terms are currently known in the art. In particular, the present method may be carried out by software, firmware, or microcode operating on a computer or computers of any type. Additionally, software embodying the present invention may comprise computer instructions in any form (e.g., source code, object code, interpreted code, etc.) stored in any computer-readable medium (e.g., ROM, RAM, magnetic media, punched tape or card, compact disc (CD) in any form, DVD, etc.). Furthermore, such software may also be in the form of a computer data signal embodied in a carrier wave, such as that found within the well-known Web pages transferred among devices connected to the Internet. Accordingly, the present invention is not limited to any particular platform, unless specifically stated otherwise in the present disclosure.

Those skilled in the art will know or be able to ascertain using no more than routine experimentation, many equivalents to the embodiments and practices described herein. Accordingly, it will be understood that the invention is not to be limited to the embodiments disclosed herein, but is to be understood from the following claims, which are to be interpreted as broadly as allowed under the law.

What is claimed is:

1. A computer-implemented method of analyzing a dataset having two or more variables, comprising:
   (i) receiving, at a network inference engine, under control of a first processor, a dataset having two or more variables;
   (ii) inferring, by the first processor, at the network inference engine, one or more global causal network computer models representative of the dataset, and each of such global causal network computer models containing equations describing the relationships between said variables, by:
      generating, at a network fragment builder, a plurality of local computer models, each local computer model describing connections between two or more of the variables in the dataset, and
      combining a plurality of the local models to generate the one or more global causal network computer models, such that the one or more global causal network computer models include two or more nodes corresponding to the two or more variables in the dataset; and
   (iii) simulating said one or more global causal network computer models, at a forward simulation engine, under control of a second processor, to predict the impact of the change made to the value of one or more first variables on the values of one or more second variables.

2. The method of claim 1, wherein (a) generating the plurality of local computer models includes (i) selecting a set of interaction forms to define the quantitative relationships between variables in said local models, (ii) building local models by proposing connections between two or more of said variables and using a scoring method, at a scoring engine, to determine a likelihood of occurrence of the local models given the dataset, and (iii) creating a library of local models ranked according to a score generated by said scoring method; and wherein (b) generating the one or more global models by choosing local models from the ranked library of local computer models and connecting said local models.

3. The method of claim 2, wherein the generating the plurality of local models includes applying a global optimization method.

4. The method of claim 3, wherein the global optimization method is metropolis Monte Carlo.

5. The method of claim 1, wherein the inferring step is constrained at least in part using prior information about the one or more variables in the dataset.

6. The method of claim 1, further comprising displaying the values of a plurality of the variables in said one or more global causal network computer models on top of or next to their corresponding representation in a graphical depiction of said one or more global causal network computer models.

7. The method of claim 6, wherein the graphical depiction is a directed acyclic graph.

8. The method of claim 1, wherein the one or more global causal network computer models are represented using Diagrammatic Cell Language.

9. The method of claim 1, wherein the one or more global causal network computer models include a consensus model comprised of two or more underlying models that together reflect a process that gave rise to the dataset.

10. The method of claim 1, wherein the global causal network computer model includes variables reflecting two or more types of measurements.

11. The method of claim 1, wherein the simulation comprises implementation of a computer script to automatically change the value of one or more said first nodes and record or display resulting values of one or more second nodes in the simulation.

12. The method of claim 1, further comprising extracting information including the mechanism of action of a drug in a biological system, wherein the dataset comprises two or more variables measuring the activity of the drug in said biological system.

13. The method of claim 1, further comprising extracting information including the identity of one or more biomarkers in a biological system, wherein the dataset comprises two or more variables measuring the activity of a drug in the biological system.

14. The method of claim 1, further comprising extracting information including the one or more pathways that connect the drug to the one or more second variables through the one or more first variables.

15. The method of claim 1, wherein the dataset includes measurements of the activity of a biological system.

16. The method of claim 15, wherein the biological system is a cell line, an animal, or a human.

17. The method of claim 1, further comprising extracting information including the mechanism of toxicity of a drug in a biological system, wherein the dataset comprises two or more variables measuring the activity of the drug in said biological system.

18. The method of claim 1, wherein the dataset includes data reflecting use of two or more drugs in substantially similar biological systems, and further comprising extracting information including the mechanism of action of the two or more drugs working together in said biological system.

19. The method of claim 1, wherein the dataset includes data reflecting use of two or more drugs in substantially similar biological systems, and further comprising extracting information including the mechanism of toxicity of the two or more drugs when used together in said biological system.

20. The method of claim 1, wherein the dataset includes data reflecting use of two or more drugs in substantially similar biological systems, two or more variables measuring the activity of the drug in the biological system, and further comprising extracting information including the identity of one or more biomarkers of the two or more drugs' efficacy together in a biological system.

21. The method of claim 1, wherein the plurality of local computer models and the one or more global causal network computer models are generated substantially simultaneously.

22. The method of claim 1, wherein a plurality of the local models are combined to form portions of the global causal network model prior to the generation of the remainder of the local computer models that comprise the global causal network models.

23. The method of claim 1, comprising inferring, at the network inference engine, an ensemble of global models including a plurality of global causal network computer models, and simulating, at the forward simulation engine, the ensemble of global models.

24. The method of claim 1, wherein simulating said global causal network computer model includes measuring, at a forward simulation engine, an impact of a change made to a value of the one or more first nodes on a value of the one or more second nodes, thereby predicting the impact of the change made to the value of one or more first variables on the values of one or more second variables.

* * * * *